US00PP20278P2

(12) United States Plant Patent
Brands et al.

(10) Patent No.: US PP20,278 P2
(45) Date of Patent: Sep. 8, 2009

(54) ***TRACHELOSPERMUM* PLANT NAMED 'SELBRA'**

(50) Latin Name: *Trachelospermum jasminoides*
Varietal Denomination: Selbra

(76) Inventors: Albrecht Brands, Paalberg 3A, 5758 SL, Neerkant (NL); Jos Selten, Hazenkampweg 21-23, 5964 PE, Horst (NL)

( * ) Notice: Subject to any disclaimer, the term of this patent is extended or adjusted under 35 U.S.C. 154(b) by 0 days.

(21) Appl. No.: 12/283,666

(22) Filed: Sep. 15, 2008

(51) Int. Cl.
*A01H 5/00* (2006.01)

(52) U.S. Cl. ..... Plt./226

(58) Field of Classification Search ..... Plt./226
See application file for complete search history.

*Primary Examiner*—Kent L Bell
(74) *Attorney, Agent, or Firm*—Penny J. Aguirre

(57) ABSTRACT

A new cultivar of *Trachelospermum jasminoides*, 'Selbra', characterized by its unique yellow flowers, its long blooming period, and its small sized leaves.

2 Drawing Sheets

Botanical classification: *Trachelospermum jasminoides*.
Varietal denomination: 'Selbra'.

BACKGROUND OF THE INVENTION

The present invention relates to a new and distinct cultivar of *Trachelospermum jasminoides* and will be referred to hereafter by its cultivar name, 'Selbra'. 'Selbra' is a new cultivar of star jasmine grown for use as a landscape plant.

The Inventor discovered 'Selbra' as a naturally occurring whole plant mutation in his garden in Neerkant, The Netherlands in June 2003. The parent plants of the new jasmine are unknown.

Asexual reproduction of the new cultivar was first accomplished by the Inventor using softwood stem cuttings in 2003 in Neerkant, The Netherlands. The characteristics of 'Selbra' have been determined to be stable and are reproduced true to type in successive generations.

SUMMARY OF THE INVENTION

The following traits have been repeatedly observed and represent the characteristics of the new cultivar as grown outdoors in trial beds and in containers in Neerkant, The Netherlands. These attributes in combination distinguish 'Selbra' as a unique cultivar of star jasmine.

1. 'Selbra' exhibits yellow flowers.
2. 'Selbra' exhibits small sized leaves.
3. 'Selbra' exhibits a long blooming period.

'Selbra' is unique for its yellow flowers, all cultivars or selections of the species *Trachelospermum jasminoides* known to the inventor have white to creamy white flowers. 'Selbra' also has smaller leaves and a longer bloom period than is typically observed for plants of *Trachelospermum jasminoides*.

BRIEF DESCRIPTION OF THE DRAWING

The accompanying colored photographs illustrate the overall appearance and distinct characteristics of 2 year-old plants of the new star jasmine as grown outdoors in 19 cm containers in Neerkant, The Netherlands.

The photograph in FIG. 1 illustrates the overall appearance of 'Selbra' in bloom.

Figure 1:
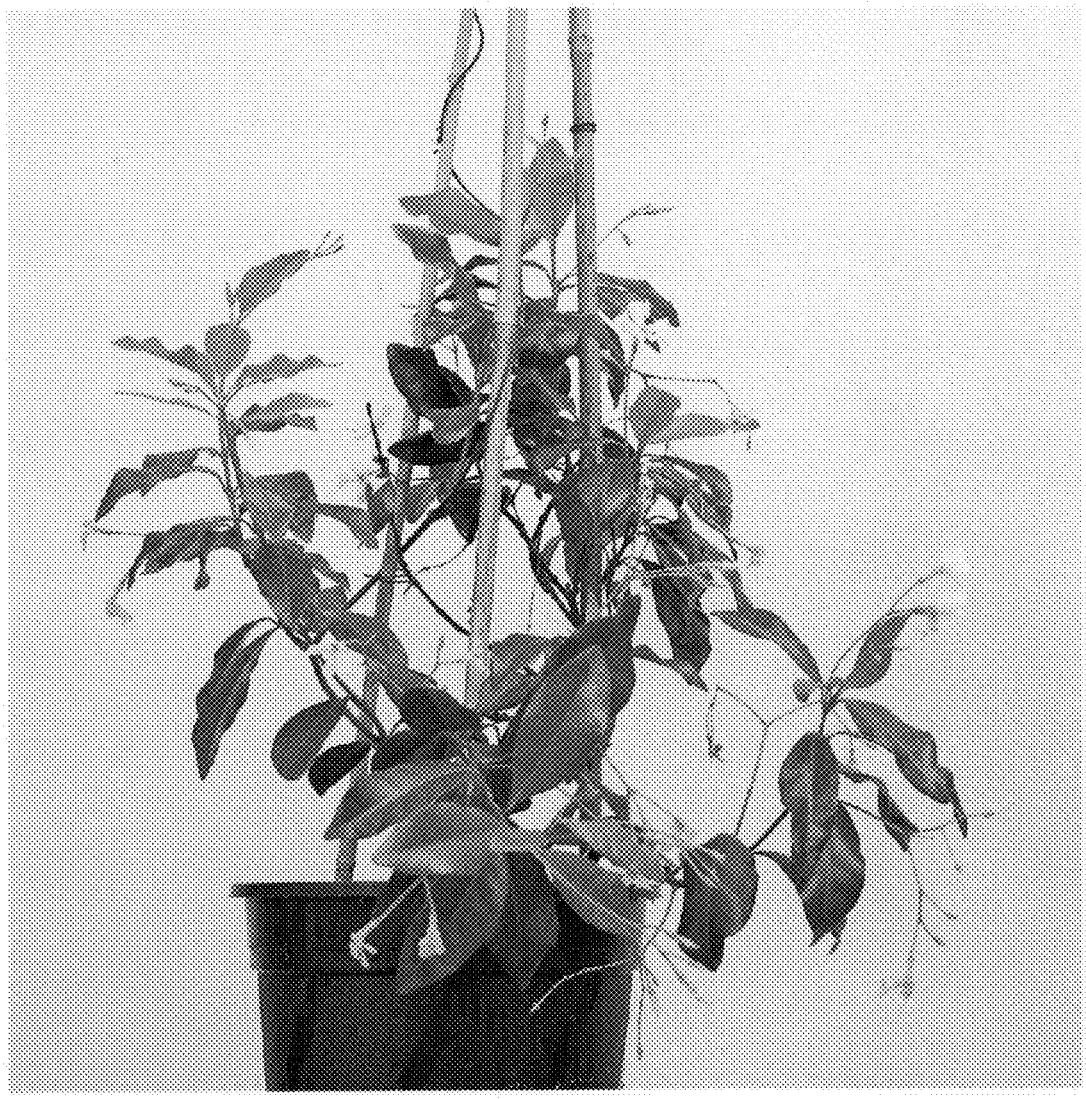
Figure 2:
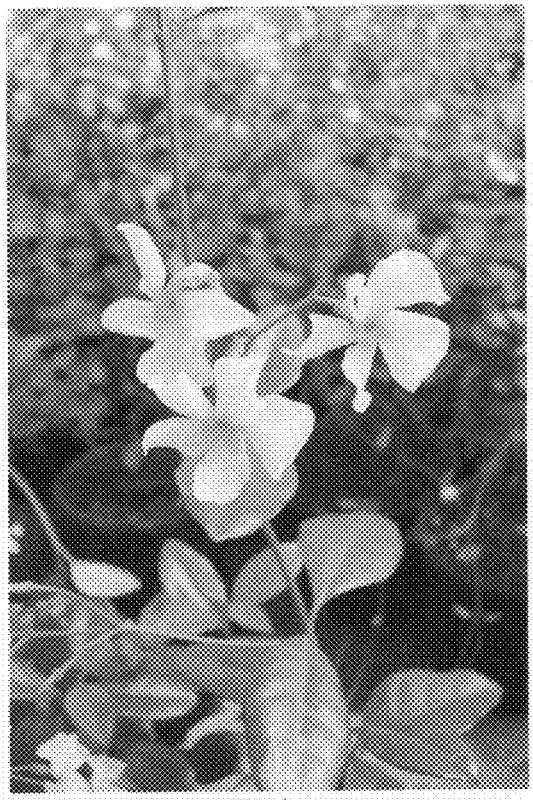

The photograph in FIG. 2 provides a close-up view of the flowers.

Figure 3:
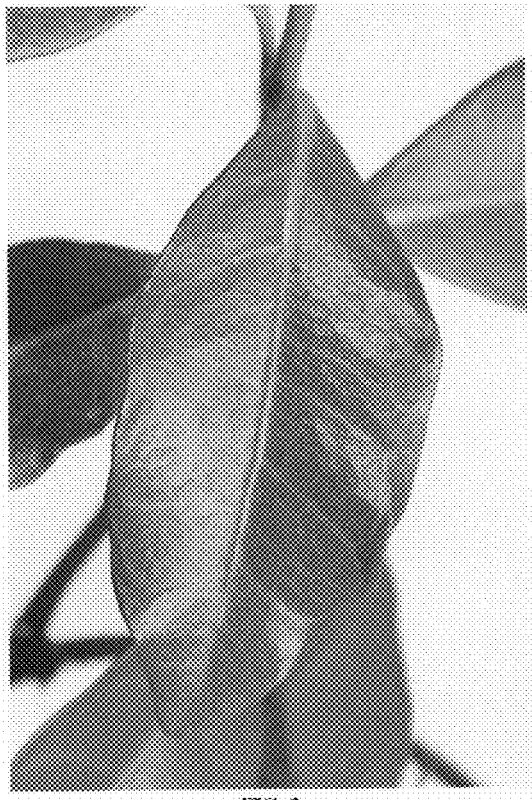

The photograph in FIG. 3 is a close-up view of a leaf of 'Selbra'.

The colors in the photographs are as close as possible with the digital photography techniques utilized and the color values cited in the detailed botanical description most accurately describe the colors of the new star jasmine.

DETAILED BOTANICAL DESCRIPTION

The following is a detailed description of 2 year-old plants of the new star jasmine as grown outdoors in 19 cm containers in Neerkant, The Netherlands. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Blooming period.*—Blooms from spring into summer in The Netherlands.

*Plant habit.*—perennial, deciduous vine.

*Height and spread.*—Reaches about 39 cm in height and 38 cm width in 2 years when held on stakes.

*Hardiness.*—At least in U.S.D.A. Zone 8a to 10.

*Diseases resistance.*—No disease problems were observed.

*Root description.*—Fibrous.

Growth and propagation:

*Propagation.*—Softwood stem cuttings.

*Root development.*—Roots develop in about 30 days at 20° C., about 12 months to finish a rooted cutting in a 13 cm container or larger.

*Growth rate.*—Vigorous.

Stem description:

*Shape.*—Round.

*Stem color.*—Young growth; 146A to 146B, mature wood N199A to N199B.

*Stem size.*—An average of 15.6 cm in length and 2.8 mm in width.

*Stem surface.*—Slightly glossy with young stems covered with short adpressed hairs; about 0.7 mm in length and 199D in color.

*Internode length.*—Average of 2.8 cm.

*Branching.*—About 10 lateral branches are produced on a 2 year-old plant.

*Other stem characteristics.*—Produces a milky fluid when damaged.

Foliage description:

*Leaf shape.*—Elliptic.

*Leaf division.*—Simple.

*Leaf base.*—Cuneate.

*Leaf apex.*—Acute.

*Leaf fragrance.*—None.

*Leaf venation.*—Pinnate, not prominent, color on upper surface 143A, color on lower surface 144A.

*Leaf margins.*—Entire, undulate.

*Leaf arrangement.*—Opposite.

*Leaf attachment.*—Petiolate.

*Leaf surface.*—Glabrous and smooth on upper and lower surface with upper surface glossy.

*Leaf texture.*—Leathery.

*Leaf size.*—Average of 7.1 cm in length and 3 cm in width.

*Leaf quantity.*—Average of 12 per lateral branch.

*Leaf color.*—New growth upper surface; 144A, new growth lower surface; 144B, mature leaves upper surface; 137A to 146A and slightly darker, mature leaves lower surface; 143C to 144A.

*Petioles.*—An average of 7.5 mm n length and 1 mm in width, 144A in color, glabrous surface.

*Stipules.*—Not present.

Inflorescence description:

*Inflorescence type.*—Axillary cyme.

*Inflorescence size.*—About 9.5 cm in depth (including peduncle) and 5.4 cm width.

*Flower buds.*—Oblanceolate in shape, about 1.5 cm in length and 4 mm in width, color is 145C with base 144C.

*Flower fragrance.*—Strong jasmine scent.

*Lastingness of flowers.*—Individual flowers last about 4 days, flowers open sequentially, self cleaning.

*Flower quantity.*—Average of 4 flowers per cyme, about 40 flowers per plant (2 years in age).

*Flower type.*—Perfect, rotate.

*Flower aspect.*—Upright to outward.

*Flower size.*—Average of 2.6 cm in diameter and 1.5 cm in depth.

*Peduncles.*—Average of 5.1 cm in length and 1 mm in diameter, 143B in color, glabrous surface, round in shape, held at about a 50% angle to stem (0% equal to flat on stem).

*Pedicels.*—Average of 1.3 cm in length and 0.8 mm in diameter, 143B in color, glabrous surface, round in shape, terminal flower held on peduncle with lateral flowers held at about a 45% angle to peduncle.

*Calyx form.*—Campanulate.

*Sepals.*—5, ovate in shape, acute apex, cuneate base, an average of 3.5 mm in length and 1.5 mm in width, entire margin, color of upper surface (immature and mature flowers); 144B, color of lower surface (immature and mature flowers); 146B to 146C, glabrous surface.

*Corolla.*—Rotate in form with lower 45% fused into a tube, propeller like in appearance.

*Petals.*—5, un-fused lobes are flabellate in shape with one side curved backwards, upper and lower surface is smooth and very slightly glossy, margin entire, fused base, broadly obtuse apex, about 2.1 cm in length and 1.1 cm in width, color of upper surface when opening; 11B to 11D with top of tube 17C, color of lower surface when opening; 11C with tube portion 153C to 153D, color of upper surface when fully open; 4D with the top of tube 13A, color of lower surface when fully open; 4D, color of both surfaces when fading; 11A.

Reproductive organs:

*Gynoecium.*—Pistil; 1, about 6 mm in length, style; average of 5.5 mm in length, 143B to 143C in color, stigma; flattened club-shaped, 144B in color, ovary; 143A in color.

*Androcoecium.*—Stamens; 5, anthers; narrow triangular in shape, an average of 3 mm in length, 153D in color, pollen; low in quantity, 4D in color.

It is claimed:

1. A new and distinct cultivar of *Trachelospermurn* plant named 'Selbra' as herein illustrated and described.

* * * * *